United States Patent
Miyazaki et al.

(10) Patent No.: US 6,482,419 B1
(45) Date of Patent: Nov. 19, 2002

(54) INORGANIC COMPOSITE POWDER AND COSMETIC COMPRISING THE SAME

(75) Inventors: Takumi Miyazaki, Kitakyushu (JP); Hirokazu Tanaka, Kitakyushu (JP)

(73) Assignee: Catalysts & Chemicals Industries Co., Ltd., Kawasaki (JP)

( * ) Notice: Subject to any disclaimer, the term of this patent is extended or adjusted under 35 U.S.C. 154(b) by 0 days.

(21) Appl. No.: 09/647,498

(22) PCT Filed: Mar. 25, 1999

(86) PCT No.: PCT/JP99/01502

§ 371 (c)(1),
(2), (4) Date: Sep. 29, 2000

(87) PCT Pub. No.: WO99/49834

PCT Pub. Date: Oct. 7, 1999

(30) Foreign Application Priority Data

Apr. 1, 1998 (JP) .............................. 10-087837

(51) Int. Cl.$^7$ .............................. A61K 6/00; A61K 7/00
(52) U.S. Cl. ..................... 424/401; 424/490; 424/64; 424/62; 424/61; 424/63; 424/400
(58) Field of Search .............. 424/401, 63, 64, 424/59, 70.7, 641, 642, 688, 490, 62, 61, 400

(56) References Cited

U.S. PATENT DOCUMENTS 5,741,355 A * 4/1998 Yamamoto et al. ......... 106/417
5,968,531 A * 10/1999 Miyoshi et al. ............. 424/401

FOREIGN PATENT DOCUMENTS

| JP | 5-17329 | 1/1993 |
| JP | 5-156174 | 6/1993 |
| JP | 5-230394 | 9/1993 |
| JP | 9-30917 | 2/1997 |
| JP | 9-30935 | 2/1997 |
| JP | 9-71417 | 3/1997 |

* cited by examiner

Primary Examiner—Thurman K. Page
Assistant Examiner—Liliana Di Nola-Baron
(74) Attorney, Agent, or Firm—Kanesaka & Takeuchi

(57) ABSTRACT

An inorganic composite powder is formed of a scaled substrate, and at least three inorganic oxide layers having different refractive indexes respectively and sequentially laminated in an order of high refractive index to low refractive index from a surface of the scaled substrate to an utmost outer layer. A refractive index of an inorganic oxide used for forming the utmost outer layer is 1.73 or less, and a difference in the refractive indexes between the utmost layer and a layer adjacent thereto is 0.6 or less. Alternatively, the thickness of at least one of a second or higher inorganic oxide layer is within ±20% of a value d given by an equation: $d=(\lambda \times X/4)/n$, wherein $\lambda$ indicates a wavelength of visual light, X indicates an odd integer, and n indicates the refractive index of the inorganic oxide.

9 Claims, No Drawings

INORGANIC COMPOSITE POWDER AND COSMETIC COMPRISING THE SAME

This application is a 371 of PCT/JP99/0152 filed Mar. 25, 1999.

FIELD OF THE INVENTION

The present invention relates to an inorganic composite powder with a coating layer comprising two or more inorganic oxides having different refractive indexes respectively and formed on a scaled substrate such as mica and to a cosmetic comprising the inorganic composite powder.

BACKGROUND TECHNOLOGY

Conventionally a scaled powder such as mica, talc, and sericite has been used for preparing make-up cosmetics such as powder foundation. The effects provided by blending of this scaled powder includes the excellent extendability of the cosmetic on the human skin, improved dispersive property of coloring pigments used therein, and its excellent capability of adhering to the human skin, so that the scaled powder is indispensable in preparation of make-up cosmetics.

These scaled powders as described above generally have a low refractive index of 1.7 or below, and when wet with oily materials blended in a cosmetic, the transparency becomes higher with the capability of covering the human skin as the ground lowered, so that it is required to blend a somewhat large quantity of titanium oxide pigment or the like in the cosmetic to compensate the defects. When a cosmetic with a somewhat large quantity of titanium oxide blended therein is used for making up, the finishing looks like that provided in daubing, which does not satisfy recent preference of users for the natural feeling of appearance.

Japanese Patent Laid-Open Publication No. 282312/1990 discloses a spherical composite powder which easily collapses when pressurized and comprises titanium oxide and silica, and discloses a cosmetic comprising mica powder prepared by coating titanium oxide and then silica thereon.

Further the present inventors proposed in the International Laid-Open Publication WO 92/03119 a composite powder prepared by depositing spherical silica with the size in the order less than a micron on a surface of a scaled substrate to homogeneously scatter light and having the effect of shading the ground. However, as this composite powder comprises silica having the low refractive index and a scaled substrate, when the composite powder is wet by oil mixed in the cosmetic, the transparency becomes higher so that the effect of covering defects on the human skin becomes disadvantageously lower.

Different from this publication, scaled substrates such as barium sulfate have been proposed from a similar view point of homogeneously scattering light, but as their refractive index is high, the requirement for the natural feeling of appearance is not sufficiently satisfied.

Further cosmetics having a satisfactory covering capability for covering such defects as blots and freckles on the human skin and insuring the feeling of transparency are proposed in Japanese Patent Laid-Open Publication No. 56628/1994 and Japanese Patent Laid-Open Publication No. 188723/1996, but these cosmetics are prepared by coating a scaly physiological pigment such mica with titanium oxide or titanium oxide containing a coloring pigment and further laminating a silica layer or a powder having the capability of scattering light thereon, and when laminated with a silica layer, a difference between a refractive index of titanium oxide and that of silica is large, and strong reflection of light occurs on the interface between the two layers, so that the feeling of transparency is not satisfactory.

DISCLOSURE OF THE INVENTION

An object of the present invention is to provide an inorganic composite powder having a satisfactory covering capability and a feeling of transparency. Another object of the present invention is to provide a cosmetic blended with the inorganic composite powder which can cover such defects as blots and freckles on the human skin and insure a natural appearance.

The inorganic composite powder according to the present invention comprises two or more types of inorganic oxides having different refractive indexes respectively and sequentially laminated from the one with the highest refractive index at the bottom on a scaled substrate, wherein the difference in the refractive index between the utmost outer layer and adjoining inner layer is 0.6 or below.

The difference in refractive indexes of all pairs of adjoining two inorganic oxide layers is preferably 0.6 or below.

Further the inorganic composite powder according to the present invention comprises two or more types of inorganic oxides having different refractive indexes respectively and sequentially laminated from the one with the highest refractive index at the bottom on a scaled substrate, wherein a thickness of at least one of the second or higher inorganic oxide layers is within ±20% of the value d given by the equation:

$$d=(\lambda \times X/4)/n$$

wherein $\lambda$ indicates a wavelength of visual light, X indicates an odd integer, and n indicates a refractive index of the inorganic oxide.

Said scaled substrate comprises preferably at least one of inorganic oxides selected from the group consisting of natural minerals such as mica, talc, and sericite; synthetic mica, synthetic sericite, plate-formed titanium oxide, plate-formed silica, plate-formed aluminum oxide, boron nitride, barium sulfate, and plate-formed titania and silica composite oxide.

The cosmetic according to the present invention is characterized in that said inorganic composite powder is blended therein and, the refractive index of the inorganic oxide used for forming the utmost outer layer of said inorganic composite powder is preferably 1.5 or below.

BEST MODE FOR CARRYING OUT THE INVENTION

Preferred embodiments of the present invention are described below.

A scaled substrate used in the present invention should preferably has an average particle diameter in the range from 2 to 20 $\mu$m and a thickness in the range from 0.05 to 1 $\mu$m. As the scaled substrate as described above, there can be enumerated such inorganic compounds as natural or synthetic mica, talc, sericite, and further plate-formed titanium oxide, plate-formed silica, plate-formed aluminum oxide, boron nitride, plate-formed barium sulfate, plate-formed titania silica composite oxide, but any other materials may be used so far as the materials have the size as described above.

The inorganic oxides which maybe used for coating the scaled substrate and refractive indexes are shown below.

Titanium oxide (2.50)
Zinc oxide (2.0)
Zirconium oxide (2.2)
Cerium oxide (2.2)
Tin oxide (2.0)
Thallium oxide (2.1)
Barium titanate (2.4)
Aluminum oxide (1.73)
Magnesium oxide (1.77)
Yttrium oxide (1.92)
Silica (1.45)
Magnesium fluoride (1.38)
magnesium carbonate (1.5)
Calcium fluoride (1.43)

In addition, a mixture of these inorganic oxides and an inorganic oxide which is a composite or a solid solution may be used for this purpose.

The inorganic composite powder according to the present invention is formed by laminating thereon two or more inorganic oxides having different refractive indexes respectively selected from those listed above from the one having a higher refractive index into two or more layers. The inorganic oxide is selected based on the covering capability required for the inorganic composite powder to be laminated therewith. To obtain an inorganic composite powder with the higher covering capability, it is preferable to use an inorganic oxide with higher refractive index such as, for instance, titanium oxide for forming the first layer. To obtain an inorganic composite powder with the lower covering capability, it is preferable to use an inorganic oxide with the intermediate covering capability such as aluminum oxide for forming the first layer.

Then, the second and higher layers are formed for lamination, and to suppress reflection of light and obtain the feeling of transparency, it is necessary that the difference of a refractive index of the inorganic oxide used for forming the utmost external layer and that of an inorganic oxide used for forming the adjoining inner layer is less than 0.6. The difference between the refractive indexes should preferably be in the range from 0.05 to 0.5.

In this invention, to further suppress reflection of light and obtain the more excellent feeling of transparency, it is desired to limit a difference between refractive indexes of adjoining layers to 0.6 or below, and. preferably to limit the difference in the range from 0.05 to 0.5. Namely, as the second layer, it is desirable to select an inorganic oxide with the refractive index different by 0.6 or less from a refractive index of the inorganic oxide used for forming the first layer, and selection of inorganic oxides for the third or higher layers should be made based on the same principle. The smaller the difference between refractive indexes of inorganic oxides used for forming the successive layers, the more ideal lamination coating can be obtained, which in turn makes it possible to obtain an inorganic composite powder which does not reflect light and has the more excellent feeling of transparency.

Even if the difference of refractive indexes between two adjoining layers in the inorganic composite powder according to the present invention is not less than 0.6, the configuration is allowable on the condition that the thickness of one of the second and higher layers is within ±20% of the value d calculated through the following equation:

$$d=(\lambda \times X/4)/n$$

wherein $\lambda$ indicates a wave length of visual light, X indicates an odd integer, and n indicates a refractive index of the inorganic oxide.

This configuration is employed because a phase of light reflected from a layer just below the one layer and a phase of light reflected from the one layer are reverse to each other and reflection of light is suppressed due to interference between the lights, and the feeling of transparency is provided.

A value in the range from 380 to 780 nm is generally employed as the wave length $\lambda$ of the visual light. For instance, to effectively weaken the reflected light in the entire wave length range of visual light, it is preferable to employ the value of 550 nm which is close to the average value of the wave lengths of visual light. Further a wave length used for the equation above can be selected based on considerations to a wave length to be reflected or that to be weakened according to a purpose in use of a cosmetic such as a preferred tone or color as well as to environment for use such as use during daytime or in evening, illumination, and colors of a costume or the like, and at the same time the thickness of a layer can be adjusted.

As a value of the integer X which is an odd number, it is generally preferable to use 1 because the thickness of a layer can be made smaller. For instance, when aluminum oxide is laminated on a layer of titanium oxide, $\lambda$ is 550 nm, and n is 1.73, so that the thickness of the aluminum oxide layer is around 80 nm.

Any method known in the art such as that in which a metal salt as a precursor of the inorganic oxide selected as described above is hydrolyzed or a prespecified quantity of an organic metal compound is hydrolyzed in alcohol medium and the hydrolytes are precipitated on a substrate or a substrate with a coating layer formed thereon may be employed for laminating an inorganic oxide.

For instance, a titanium oxide coating layer having the prespecified thickness can be obtained by dispersing a scaled substrate in water, and adding a prespecified quantity of metal salt such as titanyl sulfate into the solution for hydrolysis under alkaline atmosphere to have hydrolyte of the metal salt precipitated on a surface of the scaled substrate.

When laminating silica to form an utmost outer layer, the silica coating layer with a prespecified thickness can be formed, for instance, by adding a prespecified quantity of aqueous solution of alkali metal silicate or a prespecified quantity of organic silicon compound or the like into a dispersion of a scaled substrate with a coating layer having a higher refractive index than silica formed thereon , and further adding an acid or an alkali according to the necessity to have a silicate polymer (hydrolyzed condensate/polymer) deposited on a surface of the scaled substrate with the coating layer or layers having been formed thereon. It is noted that any other method may be employed for forming a silica coating layer.

In the present invention, the thickness of a coating film made from an inorganic oxide can be calculated from a geometrical surface area of a scaled substrate or that with an inorganic oxide coated thereon or a specific surface area measured, for instance, by means of the nitrogen adsorption method, and from a density of the inorganic oxide to be coated thereon. Further, the prespecified quantities of metal salt and organic metal compounds can be calculated from a quantity of the metal oxide to be formed thereon with the prespecified thickness.

In the present invention, it is possible to adjust the covering capability and the feeling of transparency by changing a refractive index of an inorganic oxide to be used for coating and the film thickness, which means that it is possible to adjust the covering capability and the feeling of transparency by selecting an appropriate inorganic oxide to be used for coating and its quantity. If a laminated coating film in which a difference of refractive indexes between adjoining layers is small and the refractive index of each layer becomes gradually smaller toward the utmost outer layer is obtained, a scaled inorganic composite powder reflecting light little and having the feeling of transparency and high covering capability can be obtained regardless of the thickness of the coating layer.

There is no specific limitation concerning the quantity of all inorganic oxides used for coating, but the quantity should preferably be in the range from 1 to 70 weight portions against 100 weight portions of the scaled substrate, and more preferably be in the range from 5 to 50 weight portions. If the quantity is less than 1 weight portion, the sufficient covering capability can hardly be obtained, and if the quantity is over 70 weight portions, the covering capability is too strong to insure the natural finishing, and the film thickness is too large to give comfortable feeling to the users.

With the inorganic composite powder according to the present invention, reflection of light on a surface of the scaled substrate is suppressed with the covering capability improved, so that defects of the human skin as the ground can be hid while insuring the feeling of transparency. Therefore, an inorganic composite powder having the sufficient covering capability and the feeling of transparency can be obtained.

A cosmetic according to the present invention is described below.

Although the cosmetic according to the present invention comprises the inorganic composite powder according to the present invention as described above, the cosmetic gives the feeling of transparency and can hide defects on the ground, so that it can cover the human skin without giving any damage to the natural appearance.

As for the inorganic composite powder to be blended in the cosmetic, it is preferable to use an inorganic oxide with the refractive index of 1.5 or less, and more preferably in the range from 1.5 to 1.35 for forming the utmost outer layer of the inorganic composite powder. This configuration is preferable because the refractive index of oil blended in the cosmetic is less than 1.5 and the refractive indexes of the oil and inorganic oxide are close to each other with reflection of light suppressed. The most preferable inorganic oxide used for forming the utmost outer layer is silica.

A quantity of the inorganic composite powder blended in the cosmetic according to the present invention should preferably be in the range from 1 to 90 weight percent. When the percentage is less than 1 weight %, the excellent effect can not be obtained by blending the inorganic oxide in the cosmetic, and when the percentage is more than 90 weight %, such factors as the coloring performance and oily feeling originally required for cosmetics are lost.

A surface of the inorganic composite powder according to the present invention may be processed with silicone or any fluorine compound or the like when blended in a cosmetic.

The cosmetic according to the present invention includes at least one of various components included in ordinary cosmetics including, for instance, heavy aliphatic alcohol; heavy aliphatic acids; oils such as ester oil, paraffin oil, and wax; alcohol such as ethylalcohol, propyleneglycol, sorbitol, and glycerin; moisturizing agents such as mucopolysaccharides, collagens, PCA salt, and lactates; various types of nonion-based, cation-based, anion-based, or amphoteric surface surfactants; gums such as Arabian gum, xanthane gum, polyvinyl pyrrolidone, ethylcellulose, carboxylmethylcellulose, carboxyvinyl polymer, and denatured or not-denatured clay minerals; solvents such as ethylacetate, acetone, toluene; inorganic pigments/dyes; organic pigments/dyes; BHT; chelating agents; and perfumes. Also at least one or more of inorganic fillers such as silica, talc, kaolin, mica, physiological pigments, and various types of organic resins may be included.

The cosmetic according to the present invention can be manufactured in the normal way, and may be used in various forms such as powder form, cake-like form, pencil-like form, stick form, liquid form, and cream-like form. More specifically the cosmetic includes foundation, cream, emulsion, eye-shadow, nail enamel, eye liner, mascara, lip stick, pack, and cosmetic water.

The cosmetic according to the present invention provides the advantage that it is possible to obtain a cosmetic which can cover such defects as wrinkles, blots and melasma on human skin without losing the natural appearance.

The present invention is described in detail below with reference to the examples.

EXAMPLE 1

100 g of mica was added to and well dispersed in 1 liter of demineralized water, and further 56 g of titanyl sulfate aqueous solution corresponding to 20% titanium dioxide was added to the solution, and the solution was heated, agitated, and boiled for 5 hours. Then the solution was cooled down to the room temperature and filtered. The filterate was washed with water and dried under 110° C. to obtain mica coated with titanium oxide hydrate. 100 g of mica obtained as described above was added to and well dispersed in 1 liter of demineralized water, and the solution was heated to 70° C. Then 111 g of zirconium ortho-sulfate aqueous solution corresponding to 10% zirconium oxide was gradually added to the solution keeping pH 5 with 5 weight % sodium hydroxide aqueous solution. After the addition was performed for about two hours, further 5 weight % sodium hydroxide aqueous solution was added to adjust pH 7 to pH 8, and then the solution was cooled down and filtered. The filterate was washed with water and dried under 110° C. to obtain mica coated with titanium oxide hydrate and zirconium oxide hydrate.

100 g of the mica obtained as described above was added to and well dispersed in 750 ml of demineralized water, and the solution was added to and mixed with a solution in which 11 g of aluminum chloride and 80 g of urea were dissolved in 250 ml of water, and the resultant mixture was heated to 90° C. for 5 hours, cooled down to the room temperature, and then filtered. The filterate was washed with water and dried under 110° C., and heated under 600° C. for 5 hours to obtain mica coated with titanium oxide, zirconium oxide, and aluminum oxide in this order. Further 100 g of the mica obtained as described above was added to and well dispersed in 1 liter of a mixture of ethanol and water (mixing ratio: 7 vs 3) as a solvent. Then 250 g of ethanol solution containing ortho-ethyl silicate corresponding to 4 weight % silica was added, and the solution was heated to 50° C. and kept at the temperature for about 10 hours, and then cooled and filtered. The filterate was washed with ethanol and washed sufficiently with demineralized water, and dried under 110° C. to obtain the inorganic composite powder (A) sequentially coated with titanium oxide, zirconium oxide, aluminum oxide, and silica in this order.

The inorganic composite powder (A) was actually applied to and well extended on a human skin, and the result of observation is shown in Table 1. Assessment was made by checking the feeling of transparency and invisibility of the pores on the skin, and the feeling of transparency and covering capability was assessed into four grades indicated by ⊙, ○, Δ, and X respectively. In addition to the two items for assessment, the total assessment was made taking into considerations the adhesiveness and the extendability, and the result was shown in the Table 1. Observation and assessment of the powder were similarly made also for the examples and controls described below, and the result is shown in Table 1.

EXAMPLE 2

The inorganic composite powder (B) sequentially coated with titanium oxide, zirconium oxide, and aluminum oxide in this order was obtained by following the sequence described above excluding the point that the silica coating in Example 1 was not performed.

EXAMPLE 3

The inorganic composite powder (C) sequentially coated with zirconium oxide, aluminum oxide, and silica in this order was obtained by following the sequence described above excluding the point that the coating with titanium oxide in Example 1 was not performed.

EXAMPLE 4

The inorganic composite powder (D) sequentially coated with aluminum oxide and silica in this order was obtained by following the sequence described in Example 1 excluding the point that the coating with titanium oxide and zirconium oxide in Example 1 was not performed.

EXAMPLE 5

100 g of the mica coated with titanium oxide hydrate obtained in Example 1 was added to and well dispersed in 750 ml of demineralized water, and the solution was mixed with a solution in which 25 g of aluminum chloride and 180 g of urea were dissolved in 570 ml of water, and the mixture wad heated to 90°C. and kept at the temperature for 5 hours and then cooled down to the room temperature and filtered. The filtrate was washed with water and dried under 110°C., and then heated to 600°C. for 5 hours to obtain mica sequentially coated with titanium oxide, and aluminum oxide in this order. Further, 100 g of the mica as obtained as described above was added to 1 liter of demineralized water, and the solution was well agitated. This suspension was heated to 80° C. with the pH adjusted to 9.0, and then 100 g of sodium silicate aqueous solution corresponding to 10 weight % silica was added for 5 hours maintaining pH 9.0 with hydrochloric acid solution. After the addition was finished, the solution was let as it was for one hour, and filtered. The filtrate was washed with water and dried under 110° C. for 15 hours to obtain the inorganic composite power (E) sequentially coated with titanium oxide, aluminum oxide, and silica on the mica.

EXAMPLE 6

The inorganic composite powder (F) sequentially coated with titanium oxide, zirconium oxide, aluminum oxide, silica in this order was obtained by following the same sequence as that described in Example 1 excluding the point that talc was used in place of mica used in Example 1.

EXAMPLE 7

The inorganic composite powder (G) sequentially coated with zirconium oxide, aluminum oxide, and silica in this order was obtained by following the same sequence as that described in Example 3 excluding the point that plate-formed titanium oxide with the thickness of 0.2 μm was used in place of the mica in Example 3.

EXAMPLE 8

100 g of the mica coated with titanium oxide hydrate obtained in Example 1 is added to and well dispersed in 1 liter of demineralized water, and 55 g of zinc chloride aqueous solution corresponding to 20 weight % zinc oxide and 100 g of sodium carbonate aqueous solution with the density of 10 weight % were added to the solution, and the mixture was heated under 80° C. for 5 hours, and filtered. The filtrate was washed and dried under 110° C., and then sintered under 500° C. for 3 hours to obtain mica coated sequentially with titanium oxide and zinc oxide in this order. The mica was sequentially coated with aluminum oxide and silica in the same procedure as that in Example 1 to obtain the inorganic composite powder (H) sequentially coated with titanium oxide, zinc oxide, aluminum oxide, and silica.

EXAMPLE 9

Mica coated with zirconium oxide hydrate was obtained by following the same sequence as that in Example 1 excluding the point that the coating with titanium oxide was not performed. 100 g of the coated mica was added to and well dispersed in 1 liter of water and the solution was heated to 60° C. Then 370 g of magnesium chloride aqueous solution corresponding to 3 weight % magnesium oxide was added to the solution over 8 hours adjusting the pH 10 or more with 5 weight % sodium hydroxide aqueous solution, and then the solution was neutralized with diluted sulfuric acid to adjust the pH to 8, and then cooled to the temperature and filtered. The filtrate was washed, dried under 110° C., and then sintered under 500° C. for 2 hours. By coating the material obtained as described above with silica in the same way as that described in Example 1, the inorganic composite powder (I) sequentially coated with zirconium oxide, magnesium oxide, and silica was obtained.

EXAMPLE 10

The mica coated with titanium oxide hydrate obtained in Example 1 was sintered for 3 hours under 800° C. to obtain mica coated with titanium dioxide. The mica was observed with a scanning electron microscope with the magnitude of 1000 times to measure the size of 300 particles and the average size was obtained. The specific surface area of 2.5 $m^2/g$ was calculated from the average particle size and the particle density.

By applying $\lambda=550$, $X=1$, and the refractive index of aluminum oxide n of 1.73 to the equation of $d=(\lambda \times X/4)/n$, the value d of 79.5 nm is obtained. When the specific surface area and the density of the mica coated with titanium dioxide are taken into considerations, about 55 weight portions of aluminum oxide is required for 100 weight portions of mica coated with titanium dioxide for coating the aluminum oxide with the thickness of about 80 nm. Mica sequentially coated with titanium oxide and aluminum oxide was obtained by following the same sequence as that in Example 1 excluding the point that mica coated with titanium oxide was used in place of the mica coated with titanium oxide hydrate and zirconium oxide hydrate obtained in Example 1 and mixed with a solution in which 55 g of aluminum chloride and 400 g of urea were dissolved in 1250 ml of water. Further the mica sequentially coated with titanium oxide and aluminum oxide was coated with silica in the same way as that in Example 1 to obtain the inorganic composite powder (J) sequentially coated with titanium oxide, aluminum oxide, and silica.

EXAMPLE 11

Mica coated with zirconium oxide hydrate was obtained by following the same sequence as that in Example 1 excluding the point that the coating with titanium oxide in Example 1 was not performed, and the mica was sintered for 3 hours under 800° C. to obtain mica coated with zirconium oxide. The specific surface area was calculated in the same way as in Example 10, and the specific surface area was 2.7 $m^2/g$.

By applying $\lambda=550$, $X=1$, and the refractive index of silica n of 1.45 to the equation of $d=(\lambda \times X/4)/n$, the value d of 94.8 nm is obtained. When the specific surface area and the density of the mica coated with titanium dioxide are taken into considerations, about 55 weight portions of silica oxide is required for 100 weight portions of mica coated with titanium dioxide to coat silica with the thickness of about 95 nm.

Silica was coated by following the same sequence as that in Embodiment 1 excluding the points that 100 g of mica coated with zirconium oxide was used in place of the mica sequentially coated with titanium oxide, zirconium oxide, and aluminum oxide, and that 1325 g of ethanol solution containing ortho-ethyl silicate corresponding to 4 weight percent silica was added, and the inorganic composite powder (K) sequentially coated with zirconium oxide and silica was obtained.

Control 1

The mica (P) used in Example 1 was actually applied to and fully extended on a human skin and, the result of observation is shown in Table 1.

Control 2

The mica coated with titanium dioxide hydrate obtained in Example 1 was heated under 600° C. for 5 hours to obtain the mica (Q) coated with titanium dioxide.

Control 3

The inorganic composite powder (R) sequentially coated with titanium oxide and silica was obtained by coating silica in the same way as that in Example 1 excluding the point that the mica (Q) coated with titanium dioxide obtained in Control 2 was used in place of the mica sequentially coated with titanium oxide, zirconium oxide, and aluminum oxide in Example 1.

Control 4

The talc (S) used in Example 6 was actually applied and well extended on a human skin, and the result of observation is shown in Table 1.

Control 5

The plate-formed titanium oxide (T) used in Example 7 was applied to and well extended on a human skin, and the result of observation is shown in Table 1.

Control 6

Mica coated with zirconium oxide hydrate was obtained by following the sequence in Example 1 excluding the point that ordinary mica was used in place of the mica coated with titanium oxide hydrate in Example 1. The mica was sintered for 5 hours under 600° C. to obtain mica coated with zirconium oxide. The inorganic composite powder (U) sequentially coated with zirconium oxide and silica was obtained by coating silica in the same way as that in Example 1 excluding the point that this mica coated with zirconium oxide was used in place of the mica sequentially coated with titanium oxide, zirconium oxide, and aluminum oxide.

EXAMPLE 12

A cake-like foundation comprising the following compositions was prepared by using the inorganic composite powder (A) obtained in Example 1.

| (1) | Inorganic composite powder (A) | 30 (weight portions) |
|---|---|---|
| (2) | Sericite | 36 |
| (3) | Mica | 10 |
| (4) | Titanium oxide as pigment | 5 |
| (5) | Red iron oxide | 0.4 |
| (6) | Iron oxide (yellow) | 1.6 |
| (7) | Iron oxide (black) | 0.05 |
| (8) | Sorbitan aliphatic acid ester | 2.5 |
| (9) | Stearil alcohol | 6.0 |
| (10) | Lanolin | 5.0 |
| (11) | Fluidized paraffin | 2.0 |
| (12) | Triethanol amine | 1.0 |
| (13) | Methylparaben | 0.45 |
| (14) | Perfume | Appropriately |

At first the ingredients (1) to (7) were mixed with each other. Then the ingredients (8) and (14) were well mixed and heated under 70° C., and the mixture was added to and homogeneously mixed with the former mixture. The resultant mixture was dried and pulverized to obtain particles with substantially homogeneous size, and the particles were compressed and molded.

The cake-shaped foundation was actually applied on a human skin, and the feeling of transparency was very high, yet wrinkles and pores on the skin were hardly seen, and the cosmetic film giving very natural feeling was provided.

EXAMPLE 13

Emulsion-like foundation comprising the following compositions was prepared by using the inorganic composite powder (D) obtained in Example 4.

| (1) | Demineralized water | 63.6 (weight portions) |
|---|---|---|
| (2) | 1,3-butylene glycol | 6.5 |
| (3) | Triethanol amine | 1.5 |
| (4) | Carboxymethyl cellulose | 0.2 |
| (5) | Bentonite | 0.5 |
| (6) | Inorganic composite powder (D) | 6.5 |
| (7) | Titanium oxide as pigment | 1.5 |
| (8) | Coloring pigment | Appropriately |
| (9) | Stearic acid | 4.0 |
| (10) | Monostearic acid propylene glycol | 2.0 |
| (11) | Cetostearil alcohol | 0.2 |
| (12) | Fluidized paraffin | 3.0 |
| (13) | Liquid lanolin | 2.0 |
| (14) | Myristic acid isopropyl | 8.5 |
| (15) | Methylparaben | Appropriately |
| (16) | Perfume | Appropriately |

At first, the ingredients (2) to (8) were dispersed in demineralized water (1), and the solution was heated to 75° C. The ingredients (9) to (15) were fully mixed with each other under 80° C., and the mixture was homogeneously mixed in the dispersion above. The mixture was cooled and the ingredient (16) was added thereto to obtain the emulsion-like foundation.

The emulsion-like foundation was actually applied on a human skin, and the feeling of transparency was very high, yet wrinkles and pores on the skin were hardly seen, and the cosmetic film giving very natural feeling was provided.

TABLE 1

| Powder | Transparency | Covering capability | Total assessment |
| --- | --- | --- | --- |
| A | ◎ | ◎ | ◎ |
| B | ○ | ◎ | ○ |
| C | ◎ | ◎ | ◎ |
| D | ◎ | ○ | ○ |
| E | ○ | ◎ | ○ |
| F | ◎ | ◎ | ◎ |
| G | ◎ | ◎ | ◎ |
| H | ○ | ◎ | ○ |
| I | ◎ | ◎ | ◎ |
| J | ◎ | ◎ | ○ |
| K | ◎ | ○ | ○ |
| P | ◎ | X | X |
| Q | X | ◎ | X |
| R | X | ◎ | X |
| S | ○ | X | X |
| T | X | ◎ | X |
| U | Δ | Δ | Δ |

What is claimed is:

1. An inorganic composite powder comprising:
 a scaled substrate, and
 at least three inorganic oxide layers having different refractive indexes respectively and sequentially laminated in an order of high refractive index to low refractive index from a surface of the scaled substrate to an utmost outer layer, wherein a refractive index of an inorganic oxide used for forming the utmost outer layer is 1.73 or less, and a difference in the refractive indexes between the utmost layer and a layer adjacent thereto is 0.6 or less.

2. The inorganic composite powder according to claim 1, wherein the difference in refractive indexes between any two of the layers adjacent to each other is 0.6 or less.

3. The inorganic composite powder according to claim 1, wherein said scaled substrate comprises at least one of inorganic oxides selected from the group consisting of natural mica, natural talc, natural sericite, synthetic mica, synthetic sericite, plate-formed titanium oxide, plate-formed silica, plate-formed aluminum oxide, boron nitride, barium sulfate, plate-formed titania and silica composite oxide.

4. An inorganic composite powder comprising
 a scaled substrate, and
 at least three inorganic oxide layers having different refractive indexes respectively and sequentially laminated in an order of high refractive index to low refractive index from a surface of the scaled substrate to an utmost outer layer, wherein a thickness of at least one of a second or higher inorganic oxide layer is within ±20% of a value d given by an equation:

$$d=(\lambda \times X/4)/n$$

wherein λ indicates a wavelength of visual light, X indicates an odd integer, and n indicates the refractive index of the inorganic oxide.

5. The inorganic composite powder according to claim 4, wherein said scaled substrate comprises at least one of inorganic oxides selected from the group consisting of natural mica, natural talc, natural sericite, synthetic mica, synthetic sericite, plate-formed titanium oxide, plate-formed silica, plate-formed aluminum oxide, boron nitride, barium sulfate, plate-formed titania and silica composite oxide.

6. A cosmetic comprising the inorganic composite powder according to claim 1 blended therein.

7. The cosmetic according to claim wherein the refractive index of the inorganic oxide used for forming the utmost outer layer of said inorganic composite powder is 1.5 or less.

8. A cosmetic comprising the inorganic composite powder according to claim 4 blended therein.

9. A cosmetic according to claim 8, wherein the refractive index of the inorganic oxide used for forming the utmost outer layer of said inorganic composite powder is 1.5 or less.

* * * * *